United States Patent
Tamminen et al.

(10) Patent No.: US 10,968,471 B2
(45) Date of Patent: Apr. 6, 2021

(54) METHOD OF AND ARRANGEMENT FOR TREATING BIOMASS

(71) Applicant: Sulzer Management AG, Winterthur (CH)

(72) Inventors: Janne Tamminen, Kotka (FI); Reijo Vesala, Kotka (FI); Vesa Vikman, Kotka (FI); Karl-Erik Röberg, Mölndal (SE)

(73) Assignee: SULZER MANAGEMENT AG, Winterthur (CH)

( * ) Notice: Subject to any disclaimer, the term of this patent is extended or adjusted under 35 U.S.C. 154(b) by 394 days.

(21) Appl. No.: 15/745,807

(22) PCT Filed: Sep. 28, 2016

(86) PCT No.: PCT/EP2016/073078
§ 371 (c)(1),
(2) Date: Jan. 18, 2018

(87) PCT Pub. No.: WO2017/060136
PCT Pub. Date: Apr. 13, 2017

(65) Prior Publication Data
US 2018/0216149 A1     Aug. 2, 2018

(30) Foreign Application Priority Data
Oct. 8, 2015   (EP) .................................... 15188977

(51) Int. Cl.
| | |
|---|---|
| *C12P 7/10* | (2006.01) |
| *C12P 7/08* | (2006.01) |
| *C12P 7/06* | (2006.01) |
| *C12P 19/14* | (2006.01) |
| *C13K 1/02* | (2006.01) |
| *C12M 1/00* | (2006.01) |
| *C12M 1/02* | (2006.01) |
| *C12P 19/02* | (2006.01) |

(52) U.S. Cl.
CPC ............. *C12P 19/14* (2013.01); *C12M 27/00* (2013.01); *C12M 29/00* (2013.01); *C12M 29/18* (2013.01); *C12M 45/06* (2013.01); *C12P 19/02* (2013.01); *C13K 1/02* (2013.01); *C12P 2201/00* (2013.01); *C12P 2203/00* (2013.01); *Y02E 50/10* (2013.01)

(58) Field of Classification Search
CPC ...... C12M 45/06; C12M 27/00; C12M 29/18; C12M 29/00; C12P 19/02; C12P 2201/00; C12P 19/14; C12P 2203/00; C13K 1/02; Y02E 50/16
See application file for complete search history.

(56) References Cited

U.S. PATENT DOCUMENTS

| | | | |
|---|---|---|---|
| 4,248,484 A | 2/1981 | Newcomb | |
| 5,248,484 A | 9/1993 | Scott et al. | |
| 5,348,871 A * | 9/1994 | Scott et al. | ................... 435/165 |
| 5,888,806 A | 3/1999 | Nguyen | |
| 2006/0154352 A1* | 7/2006 | Foody et al. | ................. 435/161 |
| 2009/0155064 A1 | 6/2009 | Brown et al. | |
| 2011/0177559 A1 | 7/2011 | Medoff et al. | |
| 2012/0125549 A1 | 5/2012 | Romero et al. | |

FOREIGN PATENT DOCUMENTS

| | | |
|---|---|---|
| CN | 1192800 A | 9/1998 |
| CN | 102433359 A | 5/2012 |
| CN | 103275761 A | 9/2013 |
| CN | 104619829 A | 5/2015 |
| EP | 0337394 B1 | 10/1989 |
| EP | 0368530 B1 | 5/1990 |
| EP | 0347088 B1 | 9/1994 |
| EP | 0474478 B1 | 11/1995 |
| EP | 0830511 B1 | 3/1998 |
| EP | 1147316 B1 | 3/2005 |
| RU | 2194078 C2 | 12/2002 |
| WO | 2014039984 A1 | 3/2014 |
| WO | 2014122331 A1 | 8/2014 |

OTHER PUBLICATIONS

Chinese Office Action and Search Report dated Feb. 26, 2019 in corresponding CN Patent Application No. 201680055683.6, filed Sep. 28, 2016.
International Preliminary Report on Patentability dated Oct. 4, 2017 in corresponding International Application No. PCT/EP2016/073078, filed Sep. 28, 2016.
International Search Report and Written Opinion dated Nov. 23, 2016 in corresponding International Application No. PCT/EP2016/073078, filed Sep. 28, 2016.

* cited by examiner

*Primary Examiner* — Satyendra K Singh
(74) *Attorney, Agent, or Firm* — Global IP Counsensors, LLP

(57) ABSTRACT

An arrangement for and a method of biomass hydrolysis includes a feed pump, a pre-hydrolysis reactor and a feed line there-between for feeding fresh biomass slurry to the pre-hydrolysis reactor. The feed pump is a centrifugal feed pump and the pre-hydrolysis reactor is an upflow reactor.

12 Claims, 3 Drawing Sheets

METHOD OF AND ARRANGEMENT FOR TREATING BIOMASS

CROSS-REFERENCE TO RELATED APPLICATION

This application is a U.S. National Stage application of International Application No. PCT/EP2016/073078, filed Sep. 28, 2016, which claims priority to European Application No. 15188977.1, filed Oct. 8, 2015, the contents of each of which are hereby incorporated herein by reference.

BACKGROUND

Field of the Invention

The present invention relates to a method of and an arrangement for treating biomass. The present invention is especially suitable in biomass hydrolysis, for instance, for later production of biofuels, chemicals, fertilizers etc.

Background of the Invention

The term "biomass" relates generally to any material that is derived from living, or recently living biological organisms. In the energy context it is often used to refer to plant material, however by-products and waste from livestock farming, food processing and preparation and domestic organic waste, can all form sources of biomass. Biomass is widely available and contains a high proportion of carbohydrates in the form of cellulose, hemicellulose and lignin. The five main categories of biomass are: (1) wood residues (including sawmill and paper mill discards), (2) municipal paper waste, (3) residues form bakeries and other areas of food production and processing industry, (4) agricultural residues (including corn stover and corn cobs and sugarcane bagasse), and (5) dedicated energy crops (which are mostly composed of fast growing tall, woody grasses such as switch grass and Miscanthus).

The treatment of biomass generally entails the following steps: (1) collection and transportation of the biomass to a processing plant; (2) pretreatment of the biomass with one or more of mechanical/physical, chemical, biological and thermal means to form a biomass slurry open for hydrolysis treatment; (3) performing of enzymatic, alkaline or acidic hydrolysis using highly specialized enzymes, bases or acids that catalyze the depolymerization of the carbohydrate into its component sugar molecules; (4) end treatment of the sugar molecules, like for instance fermentation of the glucose to ethanol; and (5) separation of the fermentation end product, like ethanol from the aqueous fermentation broth.

Prior art knows numerous techniques for the pretreatment of biomass material for producing substrate that may be more rapidly and efficiently hydrolyzed to yield sugar molecules.

These include, without limitation, autohydrolysis, acid hydrolysis, ammonia activation, kraft pulping, organic solvent pulping, hot water pretreatment, ammonia percolation, lime pretreatment, caustic solvent pulping, or alkali peroxide pretreatment steam explosion, i.e. the use of chemicals (e.g., with or without the addition of an acid or a base); mechanical/physical means like chopping, milling, grinding and/or refining; biological means like treatment with enzymes and/or fungi; thermal means like heating the biomass with steam, and the like. At this stage it is worthwhile understanding that two or more above listed or other appropriate pretreatments may be performed in combination for having as favorable starting material for hydrolysis as possible. A common goal of all such approaches is the use of such devices, processes and process conditions that ensure that reactants and enzymes have as open access as possible to the surface of the carbohydrate-containing solids in the biomass slurry.

After being pretreated, the biomass slurry is processed in one or more hydrolysis reactor vessel(s) where suitable chemicals or enzymes hydrolyze, e.g., break down, the carbohydrates to monomers. The pretreated biomass slurry tends to be highly viscous. During the hydrolysis, the pretreated biomass slurry is further liquefied as the polymers of the pretreated biomass are converted to monomers. The monomers, sugars, are further, after hydrolysis, processed into desired end products like for instance ethanol.

U.S. Pat. No. 5,888,806 discusses in more detail tower reactors for bioconversion of lignocellulosic material. The starting point in the US-document is the fact that prior art has taught the need for mixing the bioreactors continuously. Since continuous mixing of biomass in towers having a volume of hundreds or even one or two thousand cubic meters is nearly impossible, the US-document suggests a bioreactor tower formed of a number of cylindrical plug-flow sections and mixing zones arranged therebetween. Each mixing zone may be realized either by one or more wall mounted agitators or by an external mixing/pumping loop. The purpose for the sectioning of the tower is to allow the hydrolysis to proceed mainly in plug-flow conditions, i.e. non-mixed or non-turbulent conditions, and intermittently mixing or agitating the biomass to ensure effective and uniform heat and mass transfer. The document teaches that, in the beginning of the hydrolysis, i.e. for the first 12 hours, the mixing phases should last for about 5 minutes at two hour intervals, and thereafter for five minutes every 4-12 hours. The reason for more frequent mixing for the first 12 hours is the fact that the consistency of the biomass is high, i.e. about 10%, whereas the consistency or viscosity of the biomass gets lower when the hydrolysis reactions proceed.

To be more specific the document teaches further that wall mounted agitators are needed in the early stages of hydrolysis whereby the reactor tower, which may, in commercial scale processes, have a height of 30 to 40 meters, has to be provided with wall mounted agitators at several levels, for instance at the height of 10 meters and at the height of 20 meters. Additionally, the mixing/pumping loops has/have to be arranged at a later stage of the hydrolysis, i.e. in our example at a height of 25-30 meters. Thus the construction and instrumentation of the tower reactor with all its agitators and pumping loops, not to mention the maintenance thereof, is so complex that it, in practice, prevents the application of such tower reactors.

The US-document also teaches that the biomass that is received from its pretreatment phase is taken to a mixer where appropriate enzymes, chemicals and/or nutrients are mixed with the biomass. The document teaches that the residence time in the mixer is typically less than about 10 minutes. The mixer also serves as a pump that pushes the slurry into the bottom of the tower bioreactor and conveys the slurry through the tower. The document is silent of the mixer type, but since the residence time is counted in minutes and since the mixer acts as a pump, too, there is hardly any other option than a large-sized screw feeder. If this assumption is correct it is easy to understand why the biomass has to be mixed along the length of the tower reactor. The sole reason is the incapability of a screw feeder to mix the enzymes/chemicals/nutrients evenly in the biomass.

SUMMARY

Thus, the equipment the US-document suggests that biomass hydrolysis is complicated and, consequently, expensive. The agitators that could be used for agitating biomass having a solids loading of about 10 wt % have to be of special construction and their drive motors very powerful whereby the energy consumption for running the hydrolysis is extremely high. Also the mixers used for mixing the enzymes, chemicals and/or nutrients with the fresh biomass for minutes have to be of specific construction, which almost inevitably means, in the least, high investment costs, and obviously high miming costs, too.

US-A1-2011/0177559 discusses a process where biomass feedstocks (e.g., plant biomass, animal biomass, and municipal waste biomass) are processed to produce useful products, such as fuels. For example, systems are described that can convert feedstock materials to a sugar solution, which can then be fermented to produce ethanol. Biomass feedstock is saccharified in a vessel by operation of a jet mixer, the vessel also containing a liquid medium and a saccharifying agent.

In other words, also this more recent document teaches the need for mixing the contents of the hydrolysis reactor, i.e. the biomass slurry. A feature that needs to be understood properly is the mixing of the hydrolysis reactor of the US application by a jet mixer. A jet mixer is a device used for mixing liquids or very dilute suspensions of liquids and solids. Jet mixers are not capable of mixing hardly flowing thick and possibly lumpy suspensions. However, in view of the above cited documents, it appears that arranging some kind of a mixer in or in connection with a hydrolysis reactors is common practice. Such arrangements require one or more mixing devices, their drive and support systems, instrumentation etc., whereby both the investment, running and maintenance of the equipment form a considerable piece of the overall costs of the plant.

In practice, it appears that the basic reason, why expensive and complicated equipment are used in hydrolysis reactors, is non-equal mixing of the enzymes, nutrients, and/or chemicals in the biomass, whereby the biomass and the enzymes, nutrients, and/or chemicals therein have to be mixed or agitated during the hydrolysis a number of times.

WO-A1-2014039984 discusses a two-stage hydrolysis process where fresh biomass is pumped by means of a positive displacement pump to an enzyme mixer where enzymes are mixed with the biomass. Next the thus formed mixture of enzymes and biomass is taken to a continuously operating first downflow hydrolysis reactor. After a certain residence time biomass is discharged from the first downflow hydrolysis reactor and taken via a second enzyme mixer to a second downflow hydrolysis reactor.

Practical problems related to the above discussed hydrolysis process concern the equipment needed for running the process and the way the first hydrolysis reactor is made to operate. Firstly, the use of a positive displacement pump for moving the biomass to the first hydrolysis reactor is by no means an economical choice, the costs related to its investment, running and maintenance are each higher than those of a centrifugal pump. And secondly, the running of the first hydrolysis in a downflow mode is not economical either. In other words, pumping of the viscous biomass along a relatively narrow pipeline to the top of the first hydrolysis reactor requires a lot more energy than in a case where the reactor is an upflow reactor having a considerably larger diameter. Furthermore, running the first and the second hydrolysis reactors in a downflow mode requires that the biomass has to be, after the first hydrolysis reactor, pumped again to the top of the second hydrolysis reactor.

U.S. Pat. No. 4,248,484 discusses an attrition reactor system where a reactor vessel is coupled to a centrifugal pump used as the attritor. The basic idea is to circulate the contents of the reactor vessel via the centrifugal pump such that the attritor subjects high shear to the solids fed in the reactor vessel. The example in the patent discusses the subject attrition reactor system operating at a consistency or concentration of 1%.

An object of the present invention is to offer a solution to at least some of the above discussed problems.

Another object of the present invention is to introduce such an arrangement for biomass hydrolysis that is simple in its construction and contains very few components that need maintenance.

A further object of the present invention is to introduce such a method of and an arrangement for biomass hydrolysis that the mixing of the enzymes, nutrients, and/or chemicals is performed once or twice outside the hydrolysis reactor before feeding the mixture of biomass and the enzymes, nutrients, and/or chemicals into the hydrolysis reactor, and that the hydrolysis reaction is allowed to proceed without interruption as a plug flow.

A further object of the present invention is to introduce such a method of and an arrangement for biomass hydrolysis that the concentration of the fresh biomass is equal to or above 15%.

A further object of the present invention is to introduce such an arrangement for biomass hydrolysis that is scalable in all possible sizes.

A further object of the present invention is to introduce such an arrangement for biomass hydrolysis that is commercially attractive, i.e. in view of both investment, running and maintenance. This includes both the selection of the equipment and the operating of the equipment such that the resulting energy consumption is the smallest possible.

A further object of the present invention is to introduce such an arrangement for biomass hydrolysis that is capable of raising the solids loading of the biomass to a high level and, naturally, simultaneously reducing or, sometimes, avoiding the need for fresh water in the hydrolysis.

A yet further object of the present invention is to optimize the overall process machinery including the hydrolysis reactor.

The last object is dictated by the following facts: residence time of biomass in the hydrolysis reactor, investment related to the hydrolysis reactor and investment, running and maintenance of the equipment used for pumping and/or mixing the biomass in the hydrolysis process. When these factors are considered in detail, it is learnt that the size of the hydrolysis reactor, as it depends on both the residence time and the solids loading of the biomass slurry, should be calculated by using such a biomass slurry that has such a solids loading that the biomass slurry may be pumped by means of centrifugal pumps, which are in all aspects, i.e. investment, running and maintenance costs, superior to any other pumping equipment. Thus, even if the hydrolysis reactor has to be larger than when using, for instance, screw feeders, the investment in the larger reactor when using centrifugal pumps is very soon balanced by the lower investment, running and maintenance costs related to the use of centrifugal pumps.

At least one object of the invention is met by a method of biomass hydrolysis in a two-stage hydrolysis process having a pre-hydrolysis reactor and a hydrolysis reactor with a hydrolysis zone and a discharge zone, the method comprising the steps of pretreating fresh biomass by at least one of mechanical, physical, thermal and chemical means to open biomass for hydrolysis treatment, adding at least one of enzymes, chemicals and nutrients to the fresh biomass having a consistency of 15 wt % or above in step (a) or thereafter, mixing the at least one of enzymes, chemicals and nutrients with the fresh biomass in step (b) or thereafter to form a mixture thereof, recycling at least partially hydrolysed biomass slurry from one of the pre-hydrolysis reactor, the discharge zone of the hydrolysis reactor and the line therebetween to be mixed with the mixture of the at least one of enzymes, chemicals and nutrients and the fresh biomass in step (c) or thereafter for reducing the viscosity thereof and to form a biomass slurry, feeding the biomass slurry to the pre-hydrolysis reactor by means of a centrifugal pump, allowing the biomass slurry to advance in the pre-hydrolysis reactor in an upward direction as a laminar plug flow, and taking at least partially hydrolysed biomass slurry from the pre-hydrolysis reactor for further processing in the hydrolysis reactor.

At least one object of the invention is met by an arrangement for biomass hydrolysis comprising a feed pump, a hydrolysis reactor with an inlet and an outlet, and a feed line between the feed pump and the hydrolysis reactor for feeding fresh biomass slurry to the hydrolysis reactor, wherein the feed pump is a centrifugal feed pump and that a recycle line is arranged to extend from the outlet of the hydrolysis reactor to the feed pump or upstream thereof.

Other characterizing features typical of the present invention become evident from the accompanying description herein.

Advantages of the arrangement and method in accordance with the present invention are, for example, the following: recycling of enzymes, chemicals anchor nutrients, a commercial scale process may be built with considerably smaller investment than before, minimized use of additional water, reduced running and maintenance costs, optimized size of the hydrolysis reactor, and reliable equipment.

BRIEF DESCRIPTION OF THE DRAWINGS

The invention will be explained in more detail hereinafter with reference to the drawings.

DETAILED DESCRIPTION OF THE EMBODIMENTS

Figure 1:
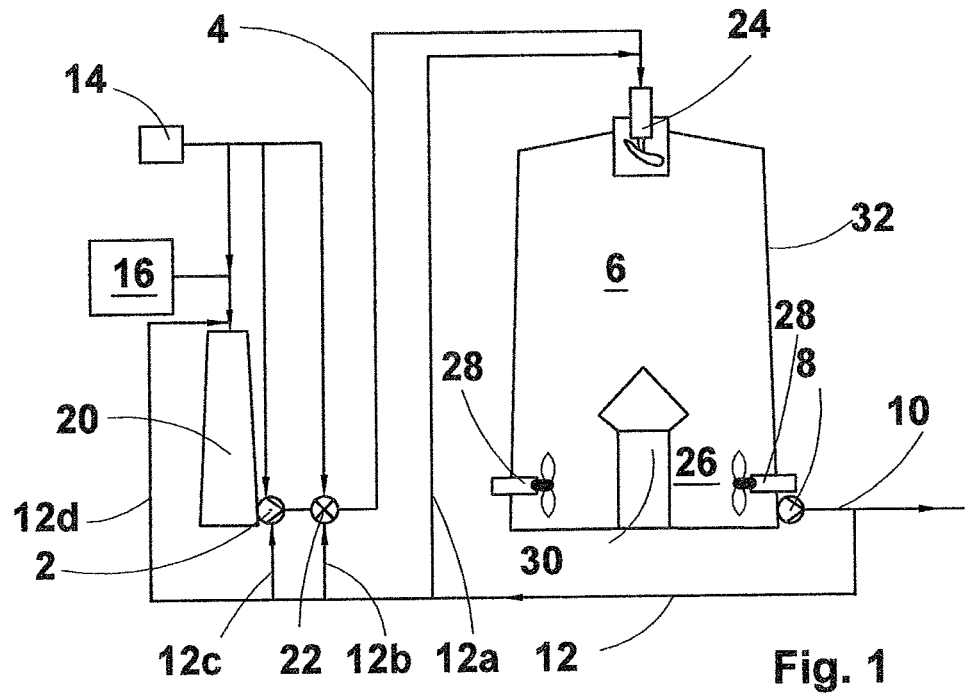
FIG. 1 illustrates schematically a first preferred embodiment of the present invention.

In accordance with FIG. 1 the main components of the arrangement for biomass hydrolysis of all the preferred embodiments of the present invention are a centrifugal feed pump 2, a feed line 4, a tower reactor, i.e. a hydrolysis reactor 6, a discharge pump 8, a discharge line 10 and a recycle line 12. The feed line 4 takes the biomass slurry from the centrifugal feed pump 2 to a first end of the tower or hydrolysis reactor 6 in connection with a second end, i.e. a discharge zone, of which a discharge pump 8 has been arranged. The discharge pump 8 moves at least partially hydrolysed biomass slurry from the tower reactor 6 via a first discharge outlet to the discharge line 10, which takes the at least partially hydrolysed biomass slurry to further processing like to a second hydrolysis stage or to fermentation, just to name a few Options without any intention to limit the further processing to the listed alternatives. The recycle line 12 branches off the discharge line 10 or the discharge pump 8 (having more than one pressure outlet), or is arranged separately by a second discharge outlet and discharge pump (not shown), for recycling a part of the at least partially hydrolysed biomass slurry to any appropriate position between the pretreatment or source 16 of biomass and the tower or hydrolysis reactor 6.

As to the centrifugal feed pump 2, a good option is a centrifugal pump designed to pump fibrous slurries or any slurries containing solid particulates. A preferred option is a so-called medium consistency pump sold and marketed by Sulzer Pumps AG, the pump being capable of pumping biomass slurry having a solids loading well above 20 wt %. Such a medium consistency pump includes a rotor extending from the pump impeller into the inlet channel of the pump or, sometimes, outside thereof into the drop leg or some other vessel upstream of the pump. The medium consistency pumps have been discussed in, for instance, EP-B1-347088, EP-B1-368530 and EP-B1-1147316. In some cases, if desired, the centrifugal feed pump 2, irrespective of its detailed construction may be provided with means for separating gas from the biomass slurry. Such pumps have been discussed in, for instance, EP-B1-337394, EP-B1-474478 and EP-B1-830511.

Additional components needed for making the arrangement work are a source 14 of one or more of enzymes, chemicals and nutrients, and a source 16 of biomass. The rest of the components shown in FIG. 1 are optional, i.e. the need therefore depends on the various factors like the solids loading, the fineness, the origin/type of the biomass, the size of the tower or hydrolysis reactor, the direction of flow in the tower reactor, i.e. upward or downward flow, etc.

Thus the drop leg 20 upstream of the feed pump 2 is needed if the flow of biomass from its pretreatment, i.e. from its source 16, is not steady but fluctuates such that a certain amount of buffer capacity is needed upstream of the centrifugal feed pump 2 so that the feed pump 2 receives a continuous flow of fresh biomass. If the flow of fresh biomass does not fluctuate, and a buffer capacity is not needed both the biomass and the enzymes, chemicals and/or nutrients may be introduced directly to the inlet of the pump 2.

A separate mixer 22 is needed if it is considered that the centrifugal pump 2 is not capable of, or for some other reason not used for, mixing all the needed enzymes, chemicals and nutrients and/or the recycled at least partially hydrolysed biomass slurry to the fresh biomass.

An inlet device 24, so called top spreader, arranged in the inlet opening or inlet of the hydrolysis reactor 6 is needed, when the tower or hydrolysis reactor 6 is a downflow one having its hydrolysis zone at its upper end and has such a large diameter that the biomass slurry is needed to be spread evenly on the plug of biomass slurry already in the tower reactor 6. Without the inlet device 24 the vertical inlet flow of biomass slurry would penetrate deep into the biomass slurry already in the tower reactor 6 and result in channeling of the biomass slurry. In this application channeling means a phenomenon where the biomass slurry entering the tower reactor with a certain velocity sinks deep into the earlier introduced biomass slurry and reaches the discharge zone of the tower reactor at a quicker pace than the rest of the biomass slurry in the tower reactor. At its worst, such a channeling could result in a part of the biomass slurry standing immovably in the tower reactor close to the wall thereof and another part of the biomass slurry passing from the inlet of the tower reactor to the discharge thereof in a relatively quick pace whereby the biomass slurry discharged from the tower reactor is substantially non-hydrolysed and the part in the tower reactor totally hydrolysed. It should also be understood that there are other options for arranging the feed of biomass slurry to the hydrolysis reactor.

A feasible option is to take the feed line 4 inside the hydrolysis reactor through the wall thereof and arrange the spreading of biomass slurry, if needed, by a spreading device positioned at the end of the feed line inside the hydrolysis reactor.

The discharge zone 26, as shown in FIG. 1, is located at the bottom part of the tower reactor 6 as the reactor is a down-flow one. When the tower or hydrolysis reactor has a diameter small enough and/or when the viscosity or the solids loading of the at least partially hydrolysed biomass slurry is low enough or the degree of hydrolysis high enough the discharge of the at least partially hydrolysed biomass slurry may be performed without any specific means, i.e. by just arranging a discharge outlet or mere outlet to the (preferably but not necessarily conical) bottom of the hydrolysis reactor. However, when the reactor 6 has a diameter wide enough and/or when the viscosity or the solids loading of the at least partially hydrolysed biomass slurry is high enough or the degree of hydrolysis low enough the discharge zone 26 of the first preferred embodiment of the present invention and illustrated in FIG. 1 includes one or more agitators 28, which keeps the at least partially hydrolysed biomass slurry in movement in the bottom part of the reactor 6 such that a continuous flow of biomass slurry enters the discharge pump 8 via the discharge outlet. The bottom part of the tower reactor or the discharge zone 26 may also include, but not necessarily, central bottom pillar 30, which, by its somewhat mushroom shape, separates the discharge zone 26 from the hydrolysis zone upper in the tower reactor 6, i.e. prevents the plug of biomass slurry from collapsing in an uncontrolled manner in the discharge zone 26. Now, the agitators 28 are preferably installed in such a manner to the wall 32 of the tower reactor that they make the at least partially hydrolysed biomass slurry rotate round the bottom pillar 30 whereby the rotating biomass slurry loosens biomass slurry in a controlled manner from the biomass slurry plug prevailing above the discharge zone 26. An option worthwhile mentioning, and especially suitable to towers or reactors having a smaller diameter, is a plow-like insert arranged on one side of the tower at the discharge zone whereby a single agitator, or a pair of agitators positioned opposite the insert to direct a flow towards the insert are able to keep the discharge zone in a movable condition such that the discharge of at least partially hydrolysed biomass slurry may proceed in a controlled manner.

As to the operation of the arrangement for biomass hydrolysis, the biomass to be introduced into the arrangement is pretreated at 16 (may be called pretreatment of biomass) by any appropriate mechanical, physical, thermal and/or chemical means or device that open the carbohydrates of the solids to enzymes, chemicals and/or nutrients used in the hydrolysis to form biomass open for the hydrolysis treatment. A preferred option for such treatment is steaming, i.e. adding steam to the biomass such that its temperature is increased and the bonds within the biomass (for instance lignin) soften and make the biomass easier to pump by a conventional ordinary or medium consistency centrifugal pump. Thus the fresh biomass entering the centrifugal feed pump 2, or the drop leg 20, if needed, is in such a fineness, i.e. divided in the pretreatment into such fine particles, that, irrespective of its solids loading or consistency being above 15 wt %, preferably above 20 wt %, it is capable of being pumped to the process by means of the centrifugal feed pump 2.

At least one of enzymes, chemicals and nutrients is added or mixed with the fresh biomass having a consistency of 15 wt % or above to form a mixture thereof in at least one of the pretreatment (at 16), the line feeding fresh biomass from the pretreatment to the drop leg 20 or to the pump 2, the pump 2 itself, the mixer 22 and at least one of the lines taking the recycled at least partially hydrolysed biomass slurry to one of the drop leg 20, the pump 2 and the mixer 22. A preferred feature of the invention is that the enzymes, chemicals and/or nutrients are introduced either dry or at as high a concentration as possible to the biomass for preventing the delivery of excess liquid into the biomass. Such an excess liquid means, in practice, waste of energy, as it has to be removed, for example by evaporation, from the end or intermediate product of the process. Thus, it is advantageous, though not totally necessary, that, after the pretreatment and mixing of enzymes, chemicals and/or nutrients with the fresh biomass, no additional liquid is added to the process.

The fresh biomass or biomass slurry also includes at least partially hydrolysed biomass slurry recycled from the discharge zone of the tower or hydrolysis reactor via line 12 and via at least one of line 12a leading to the feed line 4 (including the possibly used inlet device 24) between the feed pump 2 and the tower reactor 6, line 12b leading to the mixer 22, line 12c leading to the centrifugal feed pump 2 and line 12d leading to the line between the source or pretreatment of fresh biomass (at 16) and the drop leg 20 or the feed pump 2. Preferably the at least partially hydrolysed biomass slurry is recycled upstream of the feed pump 2 or to the feed pump itself to lower the viscosity of the fresh biomass so that it becomes pumpable or easier to pump by the centrifugal feed pump 2.

The mixing of at least one of enzymes, chemicals and nutrients is performed by the centrifugal feed pump 2 or the rotary mixer 22. In either case, the mixing takes place in a small cavity at a highly turbulent environment such that the enzymes, chemicals and/or nutrients have an optimal environment to be mixed evenly and uniformly with the fresh biomass.

The actual mixing takes place in less than 10 seconds, preferably in a few seconds, more preferably in a fractions of a second. The quick and uniform mixing in a small cavity ensures that the enzymes, chemicals and/or nutrients are evenly spread all over the biomass slurry whereby the hydrolysis may proceed efficiently up to its desired degree without any need for intermediate mixing stages.

After being provided with the recycled at least partially hydrolysed biomass slurry and at least one of enzymes, chemicals and nutrients the biomass slurry is introduced into the tower or hydrolysis reactor 6 either from top (embodiments of FIGS. 1, 2, 4 and 5) or from the bottom thereof (embodiments of FIGS. 3 and 5) depending on whether the hydrolysis reactor is a downflow one or an upflow one. The biomass slurry is introduced, in all embodiments of the present invention, to the reactor 6 such that the biomass slurry is able to advance in the reactor as a laminar plug flow so that the hydrolysis may proceed without any interruptions. 'Plug flow' is understood as a type of flow where the biomass advances in the reactor as a plug without any internal turbulence and such that the flow speed all over the cross section of the reactor is constant. When the diameter of the reactor is large and the biomass slurry is added from the top some kind of an inlet device 24 positioned in the hydrolysis reactor inlet is used. The inlet device 24 is, preferably but not necessarily, a rotary one and capable of spreading the biomass slurry as a uniform layer on top of the biomass slurry already present in the tower reactor 6, i.e. it spreads the biomass slurry evenly to the entire cross section of the tower reactor 6. If the tower or hydrolysis reactor is an upflow one, the introduction of biomass slurry into the tower may be performed by using several inlets positioned at the bottom of the tower or by arranging a specific spreading device in connection with a single inlet.

After a predetermined residence time the biomass slurry reaches the desired degree of hydrolysis, and the at least partially hydrolysed biomass slurry is discharged from the tower reactor 6. Depending mostly on the original solids loading, on the diameter of the tower reactor 6 and/or on the degree of hydrolysis the at least partially hydrolysed biomass slurry may be discharged from the discharge zone 26 of the reactor without any specific means directly via the outlet/s by at least one discharge pump 8 or by using specific means (discussed in more detail by referring to the embodiments of FIGS. 1 and 2) ensuring that the at least one discharge pump receives a continuous flow of at least partially hydrolysed biomass slurry from the reactor 6. The discharge pump 8, which is in this embodiment a centrifugal pump, pumps the at least partially hydrolysed biomass slurry to further processing.

The same discharge pump 8 or a separate discharge pump arranged to an outlet of its own is used for recycling a part of the at least partially hydrolysed biomass slurry from the discharge zone of the reactor back to be mixed with the fresh biomass slurry as discussed earlier. The purpose of recycling such biomass slurry is to prevent excess use of dilution liquid (normally water) and to maintain the solids loading of the biomass slurry in the tower reactor 6 as high as possible. The use of outside dilution liquid may be avoided as the hydrolysis reduces the viscosity of the biomass slurry by breaking carbohydrate chains to sugars, the more the further the hydrolysis is allowed to proceed. Thus, the recycled at least partially hydrolysed biomass slurry acts as a dilution liquid when mixed with the fresh biomass, in other words, it reduces the total viscosity of the fresh biomass-recycled biomass slurry mixture without introducing additional liquid in the process, whereby the resulting biomass slurry is easier to pump. Also, by using the at least partially hydrolysed biomass slurry in making the fresh biomass pumpable, the solids loading of the biomass slurry in the tower reactor is as high as possible, in fact, the solids loading is dictated by the capability of the centrifugal feed pump to pump fluid containing solids. High solids loading of the biomass slurry means, in practice, smaller size for the tower reactor compared to the hydrolysis reactor using biomass slurry having a lower solids loading. High solids loading means also smaller energy consumption in the removal of water from the end or intermediate product. Therefore, a good option for using as the discharge pump 8 is a so-called medium consistency pump sold and marketed by Sulzer Pumps AG, the pump being capable of pumping biomass slurry having a solids loading or consistency well above 20 wt %. Furthermore, the discharge pump 8, irrespective of its detailed construction, may include, if desired, a device or means for separating gas from the at least partially hydrolysed biomass slurry. An additional benefit of recycling a part of the at least partially hydrolysed biomass slurry to the fresh biomass is that simultaneously also a part of the enzymes, chemicals and/or nutrients are recycled, too, resulting in reduced need for feeding fresh enzymes, chemicals and/or nutrients from 14 to the fresh biomass slurry.

Figure 2:
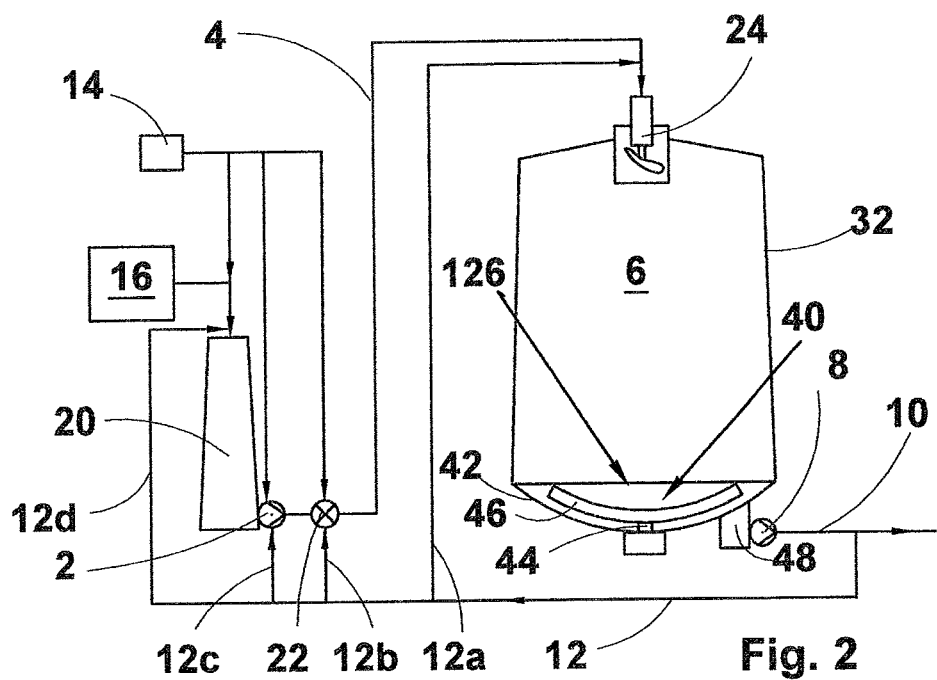
FIG. 2 illustrates schematically a second preferred embodiment of the present invention.

The second preferred embodiment of the present invention illustrated in FIG. 2 differs from the first preferred embodiment discussed in FIG. 1 at the discharge zone 126 of the tower or reactor where the tower or hydrolysis reactor 6 of FIG. 2 includes a bottom scraper 40, which is a device arranged substantially centrally to the bottom 42 of the tower reactor 6 such that a shaft 44 extends inside the reactor 6 and the shaft 44 has one or more scraper blades 46 extending outwardly from the shaft relatively close to the bottom 42 of the tower reactor 6. As another alternative, the tower bottom may include more than one scraper and (preferably but not necessarily) a central outlet for the at least partially hydrolysed biomass slurry. The tower bottom 42, or actually the outlet therein, also includes a short drop leg 48 at the lower part of which the discharge pump 8 is coupled. The bottom scraper(s) function such that while it/they is/are rotated it/they wipe the at least partially hydrolysed biomass slurry to the outlet and into the short drop leg 48, from where the biomass slurry is pumped further as discussed in connection with FIG. 1. Naturally, the recycling line 12 may have its origin in the pressurized discharge line 10, as shown in FIG. 2, but it may as well be in another pressure outlet of the discharge pump 8, or in a second discharge outlet (with another discharge pump) arranged in the short drop leg 48 or in a second short drop leg (provided with another discharge pump) arranged in a second discharge outlet in the discharge zone at the tower bottom.

A further option, not shown in the Figures, to ensure proper functioning of the discharge zone is to arrange one or more, depending on the tower diameter, tower bottom shape and/or the solids loading or the viscosity or the degree of hydrolysis of the at least partially hydrolysed biomass slurry, recycle lines taking biomass slurry from the discharge pump 8 back to the discharge zone. By recycling a part of the at least partially hydrolysed biomass slurry back to the discharge zone the flow and overall movement in the zone is increased, whereby any stagnant areas cannot be formed at the discharge zone. The introduction of the recycled at least partially hydrolysed biomass slurry may be performed through the bottom and/or the wall of the hydrolysis reactor via a desired number of inlet openings.

Figure 3:
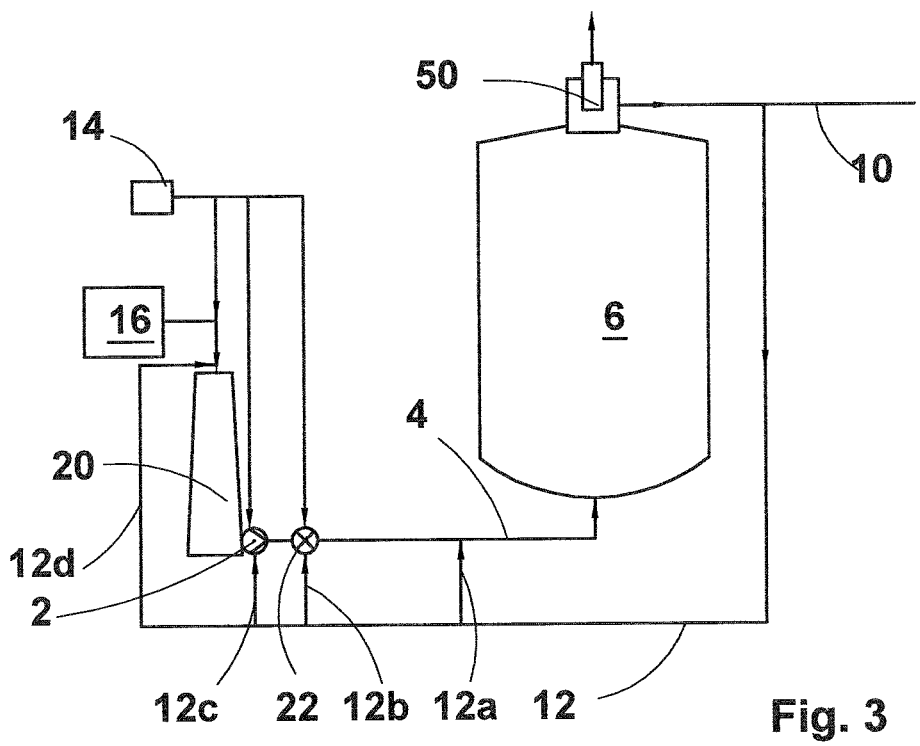
FIG. 3 illustrates schematically a third preferred embodiment of the present invention.

The third preferred embodiment of the present invention illustrated in FIG. 3 differs from the first two preferred embodiments in the flow direction in the tower or hydrolysis reactor 6, now it is an upflow reactor, i.e. the feed line 4 from the centrifugal feed pump 2 leads to an inlet opening at the bottom of the tower reactor 6, preferably at the centre thereof. Normally one inlet in the tower bottom is sufficient, but in some specific cases the feed line 4 may be provided with a flow divider, preferably close to the bottom of the tower, and, for instance, four further feed lines arranged symmetrically at the bottom of the tower bottom such that a uniform flow of biomass slurry enters the tower at four different inlets or inlet openings. This kind of an arrangement ensures that the biomass slurry advances as a laminar plug flow in an upward direction in the tower reactor.

Another difference may be seen, naturally, at the top, i.e. the discharge zone, of the tower reactor 6 where a so called top discharger 50 has been arranged in the outlet or discharge outlet. The at least partially hydrolysed biomass slurry is pressed into the top discharger 50 by the pressure created originally by the feed pump 2. The top discharger 50 comprises a chamber where a rotor rotates such that the biomass slurry flow entering the device is able to proceed to the outlet/s of the top discharger 50. The top discharger 50 is thus capable of both mixing, dividing and controlling the discharge flow of the at least partially hydrolysed biomass slurry. The rotor of the top discharger 50 may include, if desired, a device or means for creating such a centrifugal force field that is capable of removing gas from the at least partially hydrolysed biomass slurry. The separated gas may be either vented to the atmosphere or collected for further processing. The top discharger 50 may also include an impeller capable of raising pressure such that, by the created raised pressure, the at least partially hydrolysed biomass slurry is taken via line 10 to further processing, as shown, by way of example, in FIG. 5, or a part thereof recycled back to line 12. Additionally, the recycle line 12 may branch off the discharge line 10 or originate from a separate outlet of its own, i.e. in the same manner as in the earlier embodiments. In such a case that there is a separate outlet of its own for the recycle line a centrifugal pump is needed for recycling the at least partially hydrolysed biomass slurry. Naturally such a pump may also be needed though the recycled biomass slurry is taken from the discharge line 10.

Figure 4:
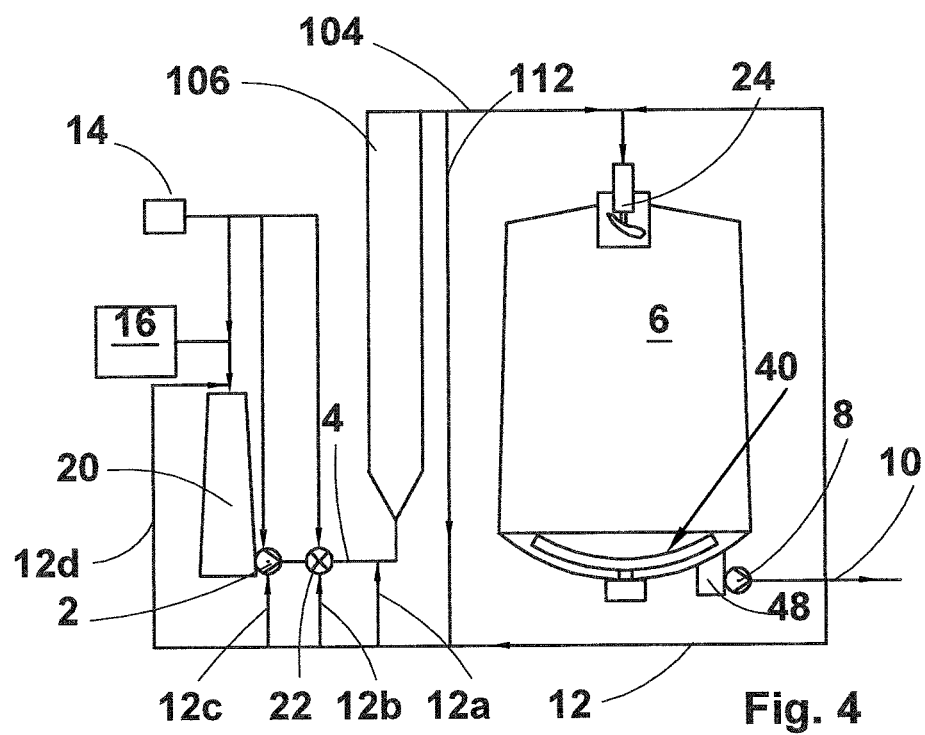
FIG. 4 illustrates schematically a fourth preferred embodiment of the present invention.

The fourth preferred embodiment of the present invention illustrated in FIG. 4 differs from the earlier embodiments by showing an upflow pre-hydrolysis reactor 106 arranged in the feed line 4 between the centrifugal feed pump 2 and the tower reactor 6, i.e. the reactors 106 and 6 are arranged in series. The upflow reactor 106 may be designed for a desired retention time for pre-hydrolysis, whereby one option is to take the recycle line 112 from the discharge line 104 between the upflow pre-hydrolysis reactor 106 and the actual tower or hydrolysis reactor 6. Another, probably more preferable, option is to branch off the recycle line from the discharge line 10 of the actual hydrolysis reactor 6 as also shown in FIG. 4. As to the discharge of the at least partially hydrolysed biomass slurry from the upflow pre-hydrolysis reactor 106 a top discharger arranged to the outlet of the pre-hydrolysis reactor 106, as discussed in connection with FIG. 3, may, preferably, be used. Another alternative, especially when the diameter of the reactor is rather small, is to arrange a bend in the reactor pipe and in such a manner connect the pre-hydrolysis reactor 106 to the inlet device 24 so that the pressure created by the feed pump 2 is capable of discharging the biomass slurry from the pre-hydrolysis reactor to the actual hydrolysis reactor 6. The discharge of the at least partially hydrolysed biomass slurry from the bottom of the tower or hydrolysis reactor 6 may be performed by means of any one of the options presented earlier in this specification, the bottom scraper 40 has been just shown as an example.

Figure 5:
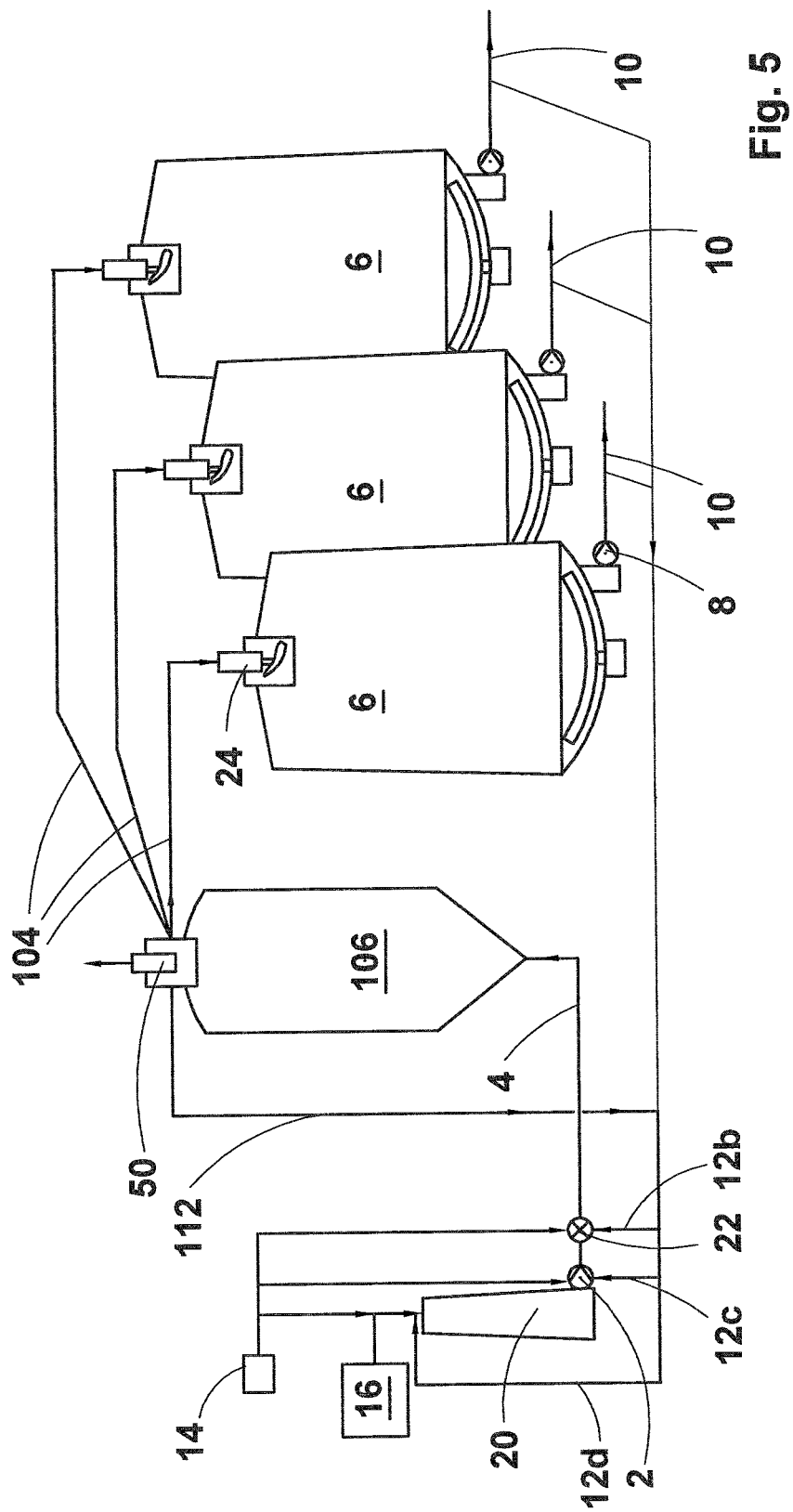
FIG. 5 illustrates schematically a fifth preferred embodiment of the present invention.

The fifth preferred embodiment of the present invention illustrated in FIG. 5 differs from the earlier embodiments in that the arrangement comprises now more than one tower or hydrolysis reactor 6. The tower reactors 6 may operate either in a continuous flow principle or in a batch principle. Otherwise the embodiment of FIG. 5 follows the principles discussed in FIG. 4, i.e. an upflow pre-hydrolysis reactor 106, which is now provided with a top discharger that divides the partially hydrolysed biomass slurry to the tower reactors 6 and to the recycle line 112. However, it is, naturally, also possible to take a part of the at least partially hydrolysed biomass slurry to the recycle line from the discharge lines 10 of the tower reactors 6.

Naturally it is also possible to use the feed pump 2, or the rotary mixer 22, if used, to divide the biomass slurry to more than one tower or hydrolysis reactor 6 arranged in parallel. In other words, the now discussed embodiment is a modification of FIG. 5 where the pre-hydrolysis reactor 106 has been deleted. Such hydrolysis reactors 6 may operate either in a continuous flow principle or in a batch principle. And the reactors 6 may be either upflow or downflow reactors, and provided with any one of the inlet and discharge means discussed earlier in this specification including an alternative where neither is actually needed.

An advantage of the embodiments illustrated in FIGS. 4 and 5 is the considerably reduced energy needed for moving the biomass through the hydrolysis process. Now, the flow resistance in the pipelines of the hydrolysis arrangement is minimized, as the use of the narrow pipelines is limited to the pipeline 4 between the pump 2 and the pre-hydrolysis reactor 106 and the pipeline 104 between the pre-hydrolysis reactor 106 and the actual hydrolysis reactor 6, whereas, in prior art using two downflow reactors, there are two narrow pipelines extending from the floor level to the top of the hydrolysis reactors.

As can be seen from the above description a method of and a novel arrangement for biomass hydrolysis have been developed. While the invention has been herein described by way of examples in connection with what are at present considered to be the most preferred embodiments, it is to be understood that the invention is not limited to the disclosed embodiments, but is intended to cover various combinations and/or modifications of its features and other applications within the scope of the invention as defined in the appended claims.

The invention claimed is:

1. A method of continuous biomass hydrolysis in a two-stage hydrolysis process having a pre-hydrolysis reactor and a hydrolysis reactor having a hydrolysis zone and a discharge zone, the method comprising:

pretreating fresh biomass by at least one of mechanical/physical, chemical, biological and thermal process or device to open the biomass for hydrolysis treatment;

adding at least one of enzymes, chemicals and nutrients to the biomass at a consistency of 15 wt % or above during the pretreating or thereafter;

mixing the at least one of enzymes, chemicals and nutrients with the fresh biomass during the adding or thereafter to form a mixture thereof;

recycling at least partially hydrolysed biomass slurry from one of the pre-hydrolysis reactor, the discharge zone of the hydrolysis reactor and a discharge line therebetween to be mixed with the mixture of the at least one of enzymes, chemicals and nutrients and the fresh biomass during the mixing or thereafter before adding to the pre-hydrolysis reactor to form a biomass slurry and to reduce the viscosity thereof;

feeding the biomass slurry to the pre-hydrolysis reactor by a centrifugal pump;

enabling the biomass slurry to advance in the pre-hydrolysis reactor in an upward direction as a laminar plug flow and form an at least partially hydrolysed biomass slurry; and taking the at least partially hydrolysed biomass slurry from the pre-hydrolysis reactor for further processing in the hydrolysis reactor.

2. The biomass hydrolysis method as recited in claim 1, further comprising mixing the partially hydrolysed biomass slurry while discharging it from the pre-hydrolysis reactor after the enabling the biomass slurry to advance.

3. The biomass hydrolysis method as recited in claim 1, wherein the mixing includes mixing by at least one of a centrifugal feed pump and a separate rotary mixer arranged in a feed line between the centrifugal feed pump and the pre-hydrolysis reactor.

4. The biomass hydrolysis method as recited in claim 1, wherein the recycling the at least partially hydrolysed biomass slurry includes recycling the at least partially hydrolysed biomass slurry to at least one of upstream of a centrifugal feed pump, the centrifugal feed pump, a rotary mixer and between the centrifugal feed pump or the rotary mixer and the pre-hydrolysis reactor.

5. The biomass hydrolysis a method as recited in claim 1, further comprising taking the recycled at least partially hydrolysed biomass slurry from the discharge line of the pre-hydrolysis reactor, from a discharge line or from the hydrolysis reactor via an outlet.

6. The biomass hydrolysis method as recited in claim 1, wherein the adding the at least one of enzymes, chemicals and nutrients includes introducing the at least one of enzymes, chemicals and nutrients to at least to one of the pretreatment of the fresh biomass, upstream of the centrifugal feed pump, the centrifugal feed pump and a separate rotary mixer.

7. The biomass hydrolysis method as recited in claim 1, further comprising separating gas from the at least partially hydrolysed biomass slurry while discharging the at least partially hydrolysed biomass slurry from the pre-hydrolysis reactor or the hydrolysis reactor.

8. The biomass hydrolysis method as recited in claim 7, wherein the separating gas from the at least partially hydrolysed biomass slurry includes separating gas by a centrifugal pump or a top discharger of the pre-hydrolysis reactor or the hydrolysis reactor.

9. The biomass hydrolysis method as recited in claim 1, further comprising separating gas from the biomass slurry while feeding the biomass slurry towards the pre-hydrolysis reactor by a centrifugal feed pump.

10. The biomass hydrolysis method as recited in claim 1, further comprising adding liquid to the biomass in the pretreatment and/or together with at least one of enzymes, chemicals and nutrients.

11. The biomass hydrolysis method as recited in claim 1, further comprising adding liquid to the biomass prior to mixing the recycled at least partially hydrolysed biomass with the fresh biomass.

12. The biomass hydrolysis method as recited in in claim 1, further comprising performing the biomass hydrolysis
    in at least one upflow pre-hydrolysis reactor and in at least one downflow hydrolysis reactor, or
    in at least one upflow pre-hydrolysis reactor and in at least two downflow hydrolysis reactors coupled in series or in parallel.

* * * * *